United States Patent [19]

Catsimpoolas

[11] Patent Number: 4,766,111
[45] Date of Patent: Aug. 23, 1988

[54] LIPIDS WITH PLASMIN INHIBITORY PROPERTIES

[75] Inventor: Nicholas Catsimpoolas, Newton Centre, Mass.

[73] Assignee: Trustees of Boston University, Boston, Mass.

[21] Appl. No.: 11,819

[22] Filed: Mar. 23, 1987

Related U.S. Application Data

[62] Division of Ser. No. 793,645, Oct. 31, 1985, Pat. No. 4,673,667.

[51] Int. Cl.$^4$ .................... A61K 31/70; A61K 31/685
[52] U.S. Cl. ........................................ 514/25; 514/78; 514/822; 514/824
[58] Field of Search .................... 514/25, 78, 822, 824

[56] References Cited

U.S. PATENT DOCUMENTS

| | | | |
|---|---|---|---|
| 3,007,787 | 9/1961 | Bianchini | 424/101 |
| 3,181,996 | 5/1965 | Bianchini | 514/56 |
| 3,985,871 | 10/1976 | Buffi et al. | 424/101 |
| 4,476,119 | 10/1984 | Della Valle et al. | 514/56 |

Primary Examiner—John Rollins
Attorney, Agent, or Firm—Felfe & Lynch

[57] ABSTRACT

Plasmin inhibitory substances have been found in mammalian omental extracts. The substances all contain lipid components. In addition, related commercially available lipid containing molecules, such as mono-, di-, and trisialogangliosides are found to possess unexpected plasmin inhibitory properties. This suggests methods of therapy for diseases and conditions where blood clotting and fibrin degradation products, are implicated.

9 Claims, 3 Drawing Sheets

LIPIDS WITH PLASMIN INHIBITORY PROPERTIES

This is a Divsional of U.S. Ser. No. 793,645, filed Oct. 31, 1985, now U.S. Pat. No. 4,673,667.

FIELD OF THE INVENTION

This invention relates to plasmin inhibitory substances, both newly derived from mammalian tissue, and commercially available. Characteristic of all of the substances is the presence of a lipid component in the plasmin inhibitory molecule.

BACKGROUND AND PRIOR ART

One of the more challenging aspects of biomedical therapy has been the treatment of diseases and conditions caused by blood clotting. The mechanism of blood clotting itself is complex, and is caused by the action of plasmin, a hemolytic enzyme, on fibrin and fibrinogen. This action produces various peptide proteolytic products, which cause vascular endothelial damage, hypoxemia, tachyphea, lung vascular injury, and so forth. In addition, fibrinolytic activity has been shown to be associated with cancer, while fibrin degradation products are believed to be produced by extracellular breakdown of fibrin by malignant cells. It has also been hypothesized that fibrin degradation products may be implicated in invation and metastasis of cancer tumors. These products have also been shown to be involved in neovascularization of tumors.

Myocardial infarctions are also recognized to be associated with elevations of fibrin degradation product content.

All of the above conditions, as well as acute thromboembolic events, venous and arterial thrombosis, intracardiac thrombosis, and systemic embolism, are conditions which are difficult to manage. Medical therapy for treating these conditions may, and usually does, involve anticoagulation therapy. One approach is to stop the underlying process of fibrinolysis, and to then rely on normal physiologic mechanisms to restore blood flow and to limit the extent of vascular obstruction or destruction of tissue.

The fibrinolysis process is fairly well know. Briefly, plasmin or plasminogen binds to fibrin, following induction by a plasminogen activator. Thorsen, *Biochim. Biophys. Acta* 393: 55–65 (1975); Lejnen, et al. *J. Biol. Chem.* 255: 10214–10222 (1980); Sahata, et al. *J.Clin.Invest.* 69: 536–542 (1982); Aoki et al., *Blood* 62: 1118–1122 (1983). Structures in the plasminogen molecule known as lysine-binding sites are involved in this binding reaction. Thorsen, supra; Wiman, et al., *Thromb. Res.* 10: 213–222 (1977).

Interference with the mechanism has been the goal of research in the field. Two glycoproteins are known to be involved with inhibition of plasminogen-fibrin binding. The plasmin inhibitor "$\alpha_2$" has been reported by Moroi, et al., *J. Biol. Chem.* 251: 5956–5965 (1976). It has been identified as a prime plasmin inhibitor in humans. Müllertz, et al., *Biochem. J.* 159: 545–553 (1976), and is recognized as a glycoprotein. Gonias, et al., *J. Biol. Chem.* 23: 14682–14685 (1983); Matsuo, et al., *Thromb. Res. 27:* 555–562 (1982); Gramse, et al., *Hoppe-Seyler's Z. Physiol. Chem.* 365(19): 19–26 (Jan. 1984); Ichinose, et al., *Biochim. Biophys. Acta* 706: 158–164 (1982).

An additional plasmin inhibitor has also been recognized, the Histidine-Rich Glycoprotein (HRG). Lipner, et al., *J. Biol. Chem.* 255: 10214–10222 (1980); Lijnen, et al., *Biochim. Biophys. Acta* 742: 109–115 (1983). Its relationship to $\alpha_2$ has been studied. Ichinose, et al., *Thromb. Res.* 33: 401–407 (1984).

Additional plasmin inhibitors have been discovered as well. Fazleabas, et al., *J. Biol. Chem.* 257(12): 6886–6897 (1982), teach a progesterone modulated plasmin inhibitor, identified as a protein. Sumi, et al., *Enzyme* 30: 252–258 (1983), teach formation of plasmin inhibitors by cyanogen bromide treatment of urinary trysin inhibitors. Levin et al., *J. Clin. Invest.* 74: 571–580 (1984) suggest that aspirin may have a role in plasmin inhibition.

U.S. Pat. No. 3,000,787, discloses a heparinoidic factor isolated from mammalian duodenum. The methods by which the factor is obtained indicate that the factor is an aminopolysaccharide, or a glycoprotein.

U.S. Pat. No. 3,181,996, discloses a heparinodic factor obtained from the pancreas. Again, the teaching indicates that the extract is a glycoprotein, or an aminopolysaccharide.

U.S. Pat. No. 3,985,871, discloses pharmaceutical compositions using the two factors, disclosed supra, in suspensions of fats, alkyl esters, and aliphatic acids.

This survey of the art shows that there is no teaching or suggestion that lipid containing molecules have plasmin inhibitory activity.

Recently, studies have been undertaken of lipid containing extracts of, the mammalian omentum. See, e.g., U.S. Pat. No. 4,699,788. These extracts have been found, unexpectedly, to be involved in numerous hemolytic physiological functions including plasmin inhibition. What is particularly surprising about the role of these lipid containing molecules is the fact that, in spite of considerable research in the field, only proteins, and glycoproteins, have been found to be plasmin inhibitors.

Plasmin is related to other protein associated enzymes, such as serine proteases, collagenases, etc. The interrelationship of these enzymes is not clear, although one factor that may be common to all of them is the need for metal ions as coenzymes.

It is an object of this invention to provide novel compositions which contain lipid containing mclecules with plasmin inhibitory properties.

It is a further object of this invention to set forth methods of treatment of diseases and conditions associated with fibrinogen degradation products, by application of the new compositions.

It is a still further object of this invention to provide new uses for old lipid containing compositions, which have now been unexpectedly found to have plamin inhibitory properties.

How these and other objects of the invention are accomplished will be seen in the accompanying details, which now follow.

DETAILED DESCRIPTION OF PREFERRED EMBODIMENTS

I. Analyzed Materials

The lipid-containing materials which were analyzed for plasmin inhibiting activity fall into two main groups: (1) fractions from mammalian omental tissue, specifically, feline tissue, and (2) known, commercially available lipid containing molecules.

The omental fractions were obtained by treating samples of mammalian omenta as follows:

Adult female cats weighing 2.4–3.2 kg. were anesthetized by an intramuscular injection of Ketamine at a preferred dosage of 7.0 mg/kg. Once anesthetized, a laparotomy was performed through a mid-line incision according to conventionally known surgical procedures. Omenta were surgically removed and placed into sterile plastic bags held at 4° C. for immediate processing. Simultaneously, subcutaneous fat was also removed and treated in a manner identical to the omental tissue for use in procedures as a non-omental lipid control. Using proper aseptic technique, the omenta were weighed, spread out onto a plastic surface and cut into individual pieces approximately four square centimeters in size using surgical scissors. These individual omental pieces, ranging in weight individually from 7 to 66 grams, were placed in a sterile Waring blender containing 300 ml of phosphate buffered saline (hereinafter "PBS") which was precooled to 4° C. The omental pieces were blended for five minutes at 20,500 rpm to yield an omental homogenate which was subsequently placed in sterile 250 ml plastic bottles and centrifuged at 1600 times gravity in a refrigerated centrifuge at 4° C. for twenty minutes. After centrifugation, three distinct and separable fractions were visible in the bottles: a pellet of mixed composition; a turbid homogenate containing substantially all the proteinaceous material, and a floating, cream colored, lipid cake. Each of these fractions was isolated individually.

The pellet of mixed composition was discarded completely. The turbid homogenate fraction was fully saturated (i.e. 100%) with aqueous ammonium sulfate which acted to precipitate the total protein in this fraction. Testing of the turbid homogenate fraction and the total protein precipitant (resuspended in PBS) by the cornea assay revealed that neither of these preparations had good angiogenic activity.

Figure 1:
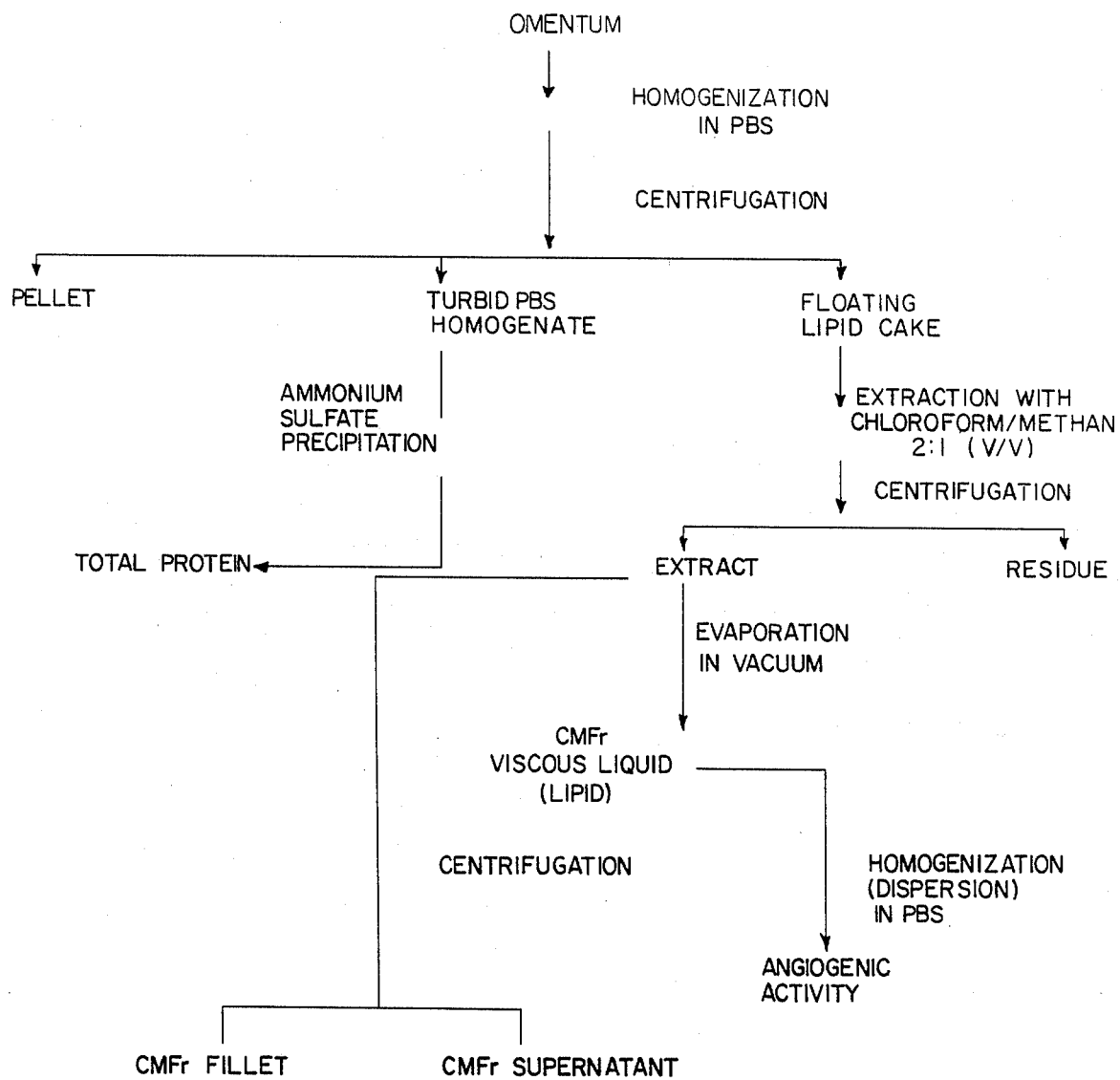
Figure 2:
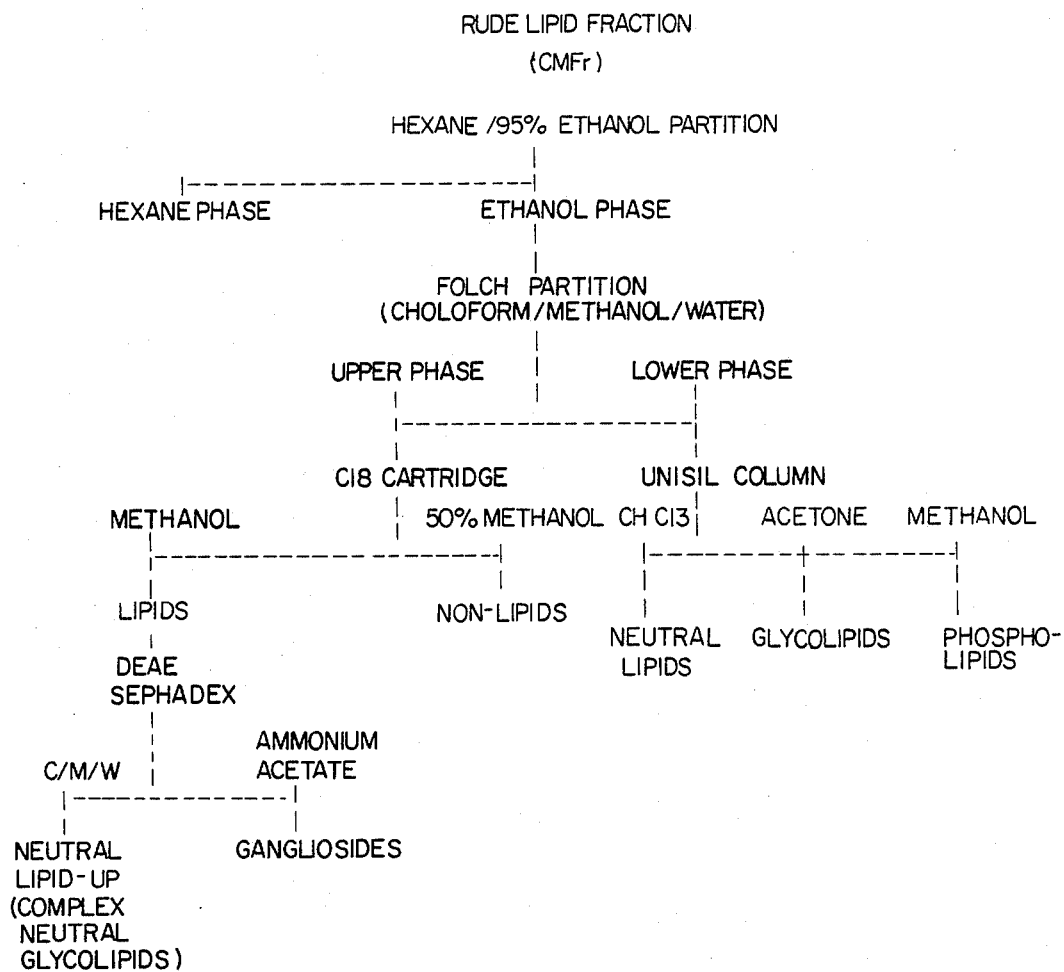

The lipid fraction isolated as a floating lipid cake was composed of two distinct layers: an upper foamy composition and a more dense, compact layer which was darker in color than the upper. Each layer was evaluated and found to contain an aotive angiogenic factor in substantial quantity. For this reason, each of these lipid layers individually and in combination comprise the active lipid fraction per se of the present invention. The weight of the lipid cake comprising both layers was found to be approximately 93% of the total weight of the omentum from which it was derived and it is this lipid cake which is used to obtain the chloroform methanol fraction described infra. The lipid cakes were combined with volumes of chloroform and methanol in a 2:1 ratio, and homogenized following centrigugation, the resulting supernatant was evaporated to remove the solvent chloroform/methanol mixture. The viscous liquid which remained is the CMFr portion. Further fractionations have also been made, as will be seen in FIGS. 1 and 2. FIGS. 1 and 2 are included to facilitate an understanding of the process by which these fractions are obtained.

The commercially available materials are sold in different purity grades. Hence, where reference is made, e.g., in the following materials to "Gangliosides Type II, III, IV, and V," this indicates that the products are purified to different degrees, but are all mixtures of various molecules classified as gangliosides, e.g.

II. Plasmin Inhibiting Assays

The substance HD-Val-Leu-Arg-pNA, which is sensitive to cleavage by plasmin, or plasmin-like serine proteases, was used as a substrate to first determine if the fractions showed plasmin activity. Each fraction was diluted 1:5 in TRIS buffer (50 mM, pH 7.4, I 0.15), and then mixed with the substrate. No detectable cleavage was found.

Following this, the samples, diluted, were incubated with normal human blood pooled plasma, which had been diluted 1:40 in TRIS buffer, in proportions of 1 part fraction to two parts plasma. These combinations were incubated to determine if the fractions had plasminogen activator properties. None were determined, with some exceptions which exhibited trace activator activity.

In a third test, each fraction was incubated with purified plasminogen so as to enhance activity, because normal human pooled plasma contains plasma proteins inhibitors. Again, no activity was observed.

The following table summarizes these results. In each of Tests 1-3, the sample was used in 1:5 dilution, and 110 l of substrate S-225 were used. In Test 2, 30 $\mu$l of a 1:40 dilution of normal human plasma were used, and in Test 3, 30 l of 40 M/L of pure plasminogen were used. The results, shown as $\Delta$mA/min, represents the average of five readings.

TABLE I

SUMMARY OF DETERMINATION OF PLASMIN/-PLASMIN-LIKE ACTIVITY, PLASMINOGEN ACTIVITY (N1 + PP), AND PLASMINOGEN ACTIVATORY ACTIVITY

| Fraction Sample | Plasmin Activity | Plasminogen Activity | Plasminogen Activatory Activity |
|---|---|---|---|
| Reference | — | — | — |
| FOLCH LP | 0 | 0 | — |
| FOLCH LP | 0 | 0 | 0 |
| FOLCH UP | 0 | 1 | 0 |
| FOLCH UP | 0 | 1 | 0 |
| DEAE-ACIDIC | 0 | 2 | 0 |
| DEAE-ACIDIC | 0 | 2 | 0 |
| HEPARIN BINDING (CMFr) | 0 | 0 | 0 |
| HEPARIN BINDING (FOLCH UP) | 0 | 0 | 0 |
| HEPARIN BINDING (FOLCH UP) | 0 | 0 | 0 |
| SILICA/IATROBEADS | 0 | 0 | 0 |
| SILICA/IATROBEADS | 0 | 0 | 0 |
| + CONTROL | 28 | 24 | 27 |
| − CONTROL | 0 | 0 | 0 |
| NHPP CONTROL | not done | 0 | not done |
| PURE PLASMINOGEN | not done | not done | 0 |
| PURE PLASMINOGEN ACTIVATED | not done | not done | 0 |
| PURE PLASMINOGEN ACTIVATED PURE PLASMINOGEN | not done | not done | 19 |
| PURE PLASMINOGEN ACTIVATED PURE PLASMINOGEN | not done | not done | 18 |

Test 1-3 were performed on various additional substances. These results are given in Table 2.

TABLE 2

| Sample | Plasmin Activity | Plasminogen Activity | Plasminogen Activatory Activity |
|---|---|---|---|
| SILICA GEL/IATROBEAD FRACTION (CAT OMENTUM) | 0 | 0 | 0 |

TABLE 2-continued

| Sample | Plasmin Activity | Plasminogen Activity | Plasminogen Activatory Activity |
|---|---|---|---|
| MIXED GANGLIOSIDES | 0 | 0 | 0 |
| DISIALOGANGLIOSIDES | 0 | 0 | 0 |
| SULFATIDES | 0 | 0 | 0 |
| CERAMIDES | 0 | 0 | 0 |
| CEREBROSIDES | 0 | 0 | 0 |
| CERAMIDE TRIHEXOSIDE | 0 | 0 | 0 |
| CERAMIDE GALACTOSIDE | 0 | 0 | 0 |
| PHOSPHATIDYL INOSITOL | 0 | 0 | 0 |
| DIGALACTOSYL DIGLYCERIDE | 0 | 0 | 0 |
| + CONTROL | .03 | .03 | .03 |
| − CONTROL | 0 | 0 | 0 |
| NHPP CONTROL | not done | 0 | not done |
| + PLG CONTROL | not done | not done | .024 |
| − PLG CONTROL | not done | not done | 0 |

These three tests show that the omental fractions used show no cleavage of HD-Val-Leu-Arg-pNA (substrate S-225), indicating that a plasmin or plasmin-like serine protease is not present. No plasminogen activator properties are seen for most of the materials either. While the FOLCH-UP and DEAE-ACIDIC fractions show trace activator activity, the reasons for this are unclear.

The constituents of the omental fractions have been identified, to some degree. Glycolipids, gangliosides, phospholipids, neutral lipids, and other lipid containing molecules are known to be present therein. Hence, not only were the omental extracts tested for plasmin inhibiting activity, but samples of known compounds were used as well.

Figure 3:
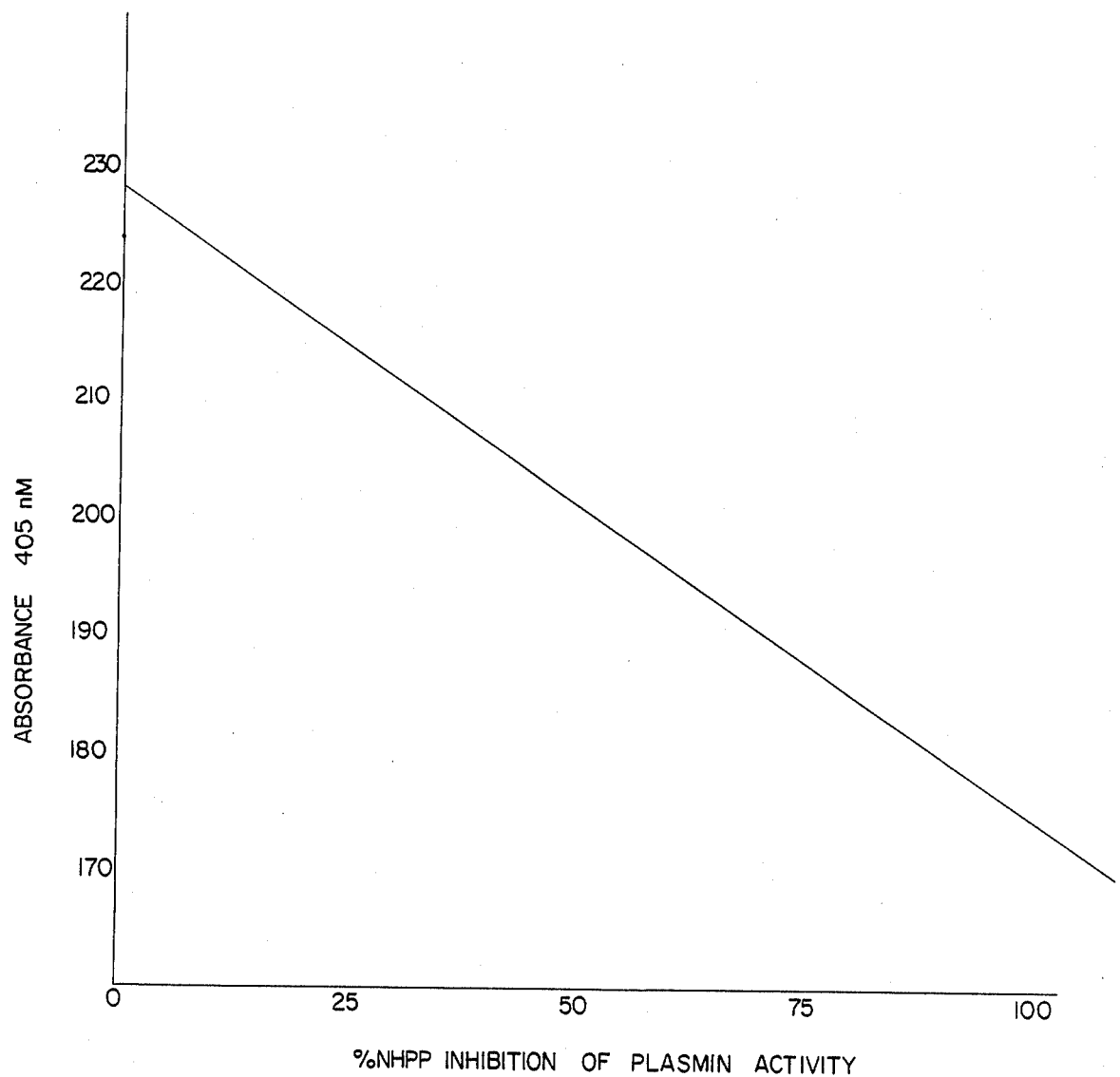

Fifty-four different runs were conducted, using various compounds and compositions. In order to determine degree of inhibition, the inhibitor activity is first derived, expressed as the percent of antiplasmin activity found in normal human pooled plasma. A standard curve is then constructed, by diluting the pooled plasma, and mixing each dilution with a known plasmin standard. Quantity of active plasmin remaining is measured and this quantity is inversely proportional to antiplasmin activity. FIG. 3 shows this, graphically.

By combining the desired sample with the NHPP, and obtaining the amount of active plasmin remaining, a comparison to the control, can be drawn. In general, if inhibition is greater than about 20%, the sample is considered a plasmin inhibitor.

In each of the following tests, 40 μl of plasmin, incubated at 37° C. for 30 seconds, 40 μl of substrate S-225, incubated for 120 seconds at 37° C., and 50 μl of 50% $CH_3COOH$ were used. Absorbances are at 405nM, and the % inhibition is by way of reference to the standard described supra.

TABLE 3

ANTIPLASMIN/PLASMIN INHIBITORY ACTIVITY

| | SAMPLE | ABSORBANCE | % INHIBITION |
|---|---|---|---|
| | Reference | — | — |
| | Standard 100% | 0.148 | |
| | Standard 75% | 0.162 | |
| | Standard 50% | 0.190 | |
| | Standard 25% | 0.227 | |
| 1 | FOLCH LP | 0.402 | 0 |
| 2 | FOLCH UP | 0.214 | 33 |
| 3 | DEAE-ACIDIC | 0.210 | 36 |
| 4 | HEPARIN BINDING-CMFr | 0.186 | 59 |
| 5 | HEPARIN BINDING-FOLCH UP | 0.190 | 55 |
| 6 | SILICA GEL/IATROBEADS | 0.008 | >100 |
| 7 | SILICA GEL/CAT OMENTUM LIPID | 0.183 | 11 |
| 8 | PURIFIED MIXED GANGLIOSIDES | 0.180 | 16 |
| 9 | PURIFIED DISIALOGANGLIOSIDES | 0.183 | 11 |
| 10 | PURIFIED SULFATIDES | 0.222 | 0 |
| 11 | PURIFIED CERAMIDES | 0.189 | 0 |
| 12 | PURIFIED CEREBROSIDES | 0.192 | 0 |
| 13 | PURIFIED CERAMIDE TRIHEXOSIDE | 0.184 | 0 |
| 14 | PURIFIED CERAMIDE GALACTOSIDE | 0.176 | 24 |
| 15 | PURIFIED PHOSPHATIDYL INOSITOL | 0.187 | 0 |
| 16 | PURIFIED DIGALACTOSYL DIGLYCERIDE | 0.190 | 0 |
| 17 | PURIFIED CERAMIDE GALACTOSIDE | 0.192 | 0 |
| 18 | PURIFIED MIXED GANGLIOSIDES | 0.189 | 0 |
| 19 | PURIFIED DISIALOGANGLIOSIDES | 0.194 | 0 |
| 20 | GANGLIOSIDES "TYPE II" | 0.177 | 15 |
| 21 | GANGLIOSIDES "TYPE III" | 0.174 | 17 |
| 22 | GANGLIOSIDES "TYPE IV" | 0.180 | 13 |
| 23 | GANGLIOSIDES "TYPE V" | 0.189 | — |
| 24 | CERAMIDES "TYPE III" | 0.186 | — |
| 25 | CERAMIDES "TYPE IV" | 0.162 | 25 |
| 26 | CEREBROSIDES "TYPE I" | 0.174 | 18 |
| 27 | CEREBROSIDES "TYPE II" | 0.189 | 0 |
| 28 | GLUCOCEREBROSIDES | — | — |
| 29 | SULFATIDES | 0.183 | — |
| 30 | SPHINGOMYELIN | 0.174 | 18 |
| 31 | PHOSPHATIDYL CHOLINE | 0.224 | — |
| 32 | TRISIALOGANGLIOSIDES | 0.213 | 13 |
| 33 | CMFr (CAT OMENTUM) | 0.223 | — |
| 34 | HEXANE PHASE (CAT OMENTUM) | 0.225 | — |
| 35 | ETHANOL PHASE (CAT OMENTUM) | 0.225 | — |
| 36 | FOLCH UP | 0.217 | 10 |
| 37 | FOLCH LP | 0.225 | — |
| 38 | FELINE MONOSIALOGANGLIOSIDE | 0.214 | 14 |
| 39 | FELINE DISIALOGANGLIOSIDES | 0.167 | 85 |

TABLE 3-continued

ANTIPLASMIN/PLASMIN INHIBITORY ACTIVITY

| | SAMPLE | ABSORBANCE | % INHIBITION |
|---|---|---|---|
| 40 | FELINE TRISIALOGANGLIOSIDES | 0.219 | 0 |
| 41 | DISIALOGANGLIOSIDES | 0.206 | 25 |
| 42 | TRISIALOGANGLIOSIDES | 0.121 | >100 |
| 43 | MIXED GANGLIOSIDES | 0.208 | 23 |
| 44 | GLOBOSIDES | 0.191 | 49 |
| 45 | SULFATIDES | Turbid | — |
| 46 | PHOSPHOINOSITIDES | Turbid | — |
| 47 | PHOSPHATIDYL INOSITOL 4-5 DIPHOSPHATE | Turbid | — |
| 48 | PHOSPHATIDYL INOSITOL 4-MONOPHOSPHATE | Turbid | — |
| 49 | CERAMIDES "TYPE III" | 0.214 | 14 |
| 50 | CERAMIDES "TYPE IV" | 0.215 | 14 |
| 51 | CEREBROSIDES "TYPE I" | 0.224 | 0 |
| 52 | CEREBROSIDES "TYPE II" | 0.214 | 14 |
| 53 | SPHINGOMYELIN | Turbid | — |
| 54 | TRISIALOGANGLIOSIDES | 0.165 | >100 |

As will be seen from the tables, trisialogangliosides how the greastest degree of plasmin inhibition. To study his further, tests were run, using various dilutions. hese are summarized in Table 4.

TABLE 4

PLASMIN INHIBITION BY TRISIALOGANGLIOSIDES

| DILUTION | ABSORBANCE | % INHIBITION |
|---|---|---|
| 1:5 | 0.165 | >100 |
| 1:10 | 0.198 | 69 |
| 1:20 | 0.208 | 50 |
| 1:40 | 0.225 | 25 |
| 1:60 | 0.228 | 18 |
| 1:80 | 0.229 | 18 |
| 1:100 | 0.234 | 0 |

The results show that various lipid containing molecules have plasmin inhibitory effects. Particularly worthwhile are the trisialogangliosides.

Even in dilutions as great as 1:80, these possess inhibitory characteristics which classify them as plasmin inhibitors. (In general, inhibition of 20% or more is arbitrarily chosen as the lower limit for plasmin inhibition).

The effect of these lipid containing molecules on plasmin is shown by Test 3. By analogy, the compounds and compositions may work in similar fashion on similar enzymes, such as the serine protease family of enzymes, collagenases, and so forth.

Various diseases and conditions are associated with fibrin degradation products, and excess plasmin activity. Vascular endothelial diseases, hypoxemia, tachyphea, lung vascular injury, metastasis and invasion of cancer tumors, coronary thrombosis, pulmonary embolisms, and related conditions are all associated with plasmin activity. The compositions of this invention may be used to treat these conditions. They are natural products, especially the omental extracts, are readily available, and the amounts and type of treatment developed can easily be varied depending upon the nature of the condition being treated.

The terms and expressions which have been employed are used as terms of description and not of limitatior, and there is no intention in the use of such terms and expressions of excluding any equivalents of the features shown and described or portions thereof, it being recognized that various modifications are possible within the scope of the invention.

I claim:

1. A method of treating conditions characterized by excess plasmin activity comprising administering an effective amount of a pharmaceutically acceptable plasmin inhibiting cerebrosive, globoside, ceramide glycoside or sphingomyelin to a subject with a condition characterized by excess plasmin activity under conditions favoring inhibition of plasmin activity by said plasmin inhibiting cerebroside, glyoboside, ceramide glycoside or sphingomyelin.

2. A method as in claim 1, wherein said cerebroside, globoside, ceramide glycoside or sphingomyelin is administered to a human being.

3. A method as in claim 1, wherein said disease is characterized by vascular-endothelial damage, hypoxemia, tachiphea, or vascular injury.

4. A method as in claim 1, wherein said disease is characterized by excessive fibrin or fibrin degradation products.

5. A method as in claim 1, wherein said cerebroside, glyboside, ceramide glycoside or sphingomyelin is administered in intervenous, intramuscular, topical, or oral form.

6. A method as in claim 1, wherein a cerebroside is administered to said subject.

7. A method as in claim 1, wherein a globoside is administered to said subject.

8. A method as in claim 1, wherein a ceramide glycoside is administered to said subject.

9. A method as in claim 1, wherein a sphingomyelin is administeried to said subject.

* * * * *